US006495180B1

(12) United States Patent
Gurol

(10) Patent No.: US 6,495,180 B1
(45) Date of Patent: Dec. 17, 2002

(54) ACID REDUCED WHOLE BEAN COFFEE AND PROCESS

(75) Inventor: Ismail Macit Gurol, Seattle, WA (US)

(73) Assignee: TAMER International, Ltd., Seattle, WA (US)

( * ) Notice: Subject to any disclaimer, the term of this patent is extended or adjusted under 35 U.S.C. 154(b) by 0 days.

(21) Appl. No.: 09/514,411

(22) Filed: Feb. 28, 2000

Related U.S. Application Data

(63) Continuation-in-part of application No. 09/089,927, filed on Jun. 3, 1998, now Pat. No. 6,045,843, which is a continuation-in-part of application No. 08/772,168, filed on Dec. 20, 1996, now Pat. No. 6,066,342, which is a continuation-in-part of application No. 08/577,147, filed on Dec. 22, 1995, now Pat. No. 5,853,787.
(60) Provisional application No. 60/156,622, filed on Sep. 27, 1999.

(51) Int. Cl.[7] ............................... A23F 5/00; A23F 5/10
(52) U.S. Cl. ...................... 426/309; 426/509; 426/629; 426/594
(58) Field of Search ........................ 426/594, 509, 426/629, 309

(56) References Cited

U.S. PATENT DOCUMENTS

| 243,521 A | 6/1881 | Davidson |
|---|---|---|
| 256,082 A | 4/1882 | Von Hofman |
| 312,516 A | 2/1885 | Schilling |
| 680,889 A | 8/1901 | Schutz |
| 832,322 A | 10/1906 | Jurgens et al. |
| 1,137,265 A | 4/1915 | Hübner |
| 1,742,261 A | 1/1930 | Klein |
| 1,822,227 A | 9/1931 | Lendrich et al. |
| 2,036,345 A | 4/1936 | Merkel |
| 2,419,031 A | 4/1947 | Pollack |
| 2,477,080 A | 7/1949 | Necheles et al. |
| 2,518,441 A | 8/1950 | Schaeppi et al. |
| 2,626,558 A | 1/1953 | Stein |
| 2,687,355 A | 8/1954 | Benner et al. |
| 2,889,226 A | 6/1959 | Hinkley |
| 3,495,988 A | 2/1970 | Balassa |
| 3,644,122 A | 2/1972 | Yeransian |
| 3,984,571 A | 10/1976 | Chen |
| 4,104,370 A | 8/1978 | Bloch |
| 4,317,841 A | 3/1982 | Brambilla et al. |
| 4,327,076 A | 4/1982 | Puglia et al. |
| 4,461,778 A | 7/1984 | Vialatte née Geolier |
| 4,514,389 A | 4/1985 | Miyata |
| 4,576,819 A | 3/1986 | Miyata et al. |
| 4,755,385 A | 7/1988 | Etienne et al. |
| 4,801,608 A | 1/1989 | Bos et al. |
| 4,857,332 A | 8/1989 | Schricker |
| 4,904,473 A | 2/1990 | Schricker et al. |
| 4,976,963 A | 12/1990 | Schricker et al. |
| 4,976,983 A | 12/1990 | Hirsh et al. |
| 4,985,271 A | 1/1991 | Neilson et al. |
| 5,147,666 A | 9/1992 | Doonan et al. |
| 5,229,155 A | 7/1993 | Weisemann et al. |
| 5,306,511 A | 4/1994 | Whang |
| 5,314,852 A | 5/1994 | Klatte |
| 5,350,591 A | 9/1994 | Canton |
| 5,461,082 A | 10/1995 | Machimura et al. |
| 5,498,426 A | 3/1996 | Wilson et al. |
| 5,518,743 A | 5/1996 | Pergola et al. |

FOREIGN PATENT DOCUMENTS

| EP | 655586 | 12/1982 |
|---|---|---|
| GB | 02166336 | 5/1986 |
| JP | 56-133027 | 10/1981 |
| JP | 61-19453 | 1/1986 |
| JP | 61-92534 | 5/1986 |
| JP | 63-146753 | 6/1988 |
| JP | 02-219542 | 9/1990 |

OTHER PUBLICATIONS

Barrett–Connor, E., et al., "Coffee–Associated Osteoporosis Offset by Daily Milk Consumption," *Journal of the American Medical Association*, Jan. 26, 1994, vol. 271, No. 4, pp. 280–283.
"Ground Coffee," *Consumer Reports*, Jan. 1991, pp. 30–50.
Hornstein, I., "Flavor Chemistry," symposium, American Chemical Society, Detroit, MI, 1966, pp. 180–187.
Peterson, M.S., et al., *Encyclopedia of Food Science*, 1978, pp. 1–6.
Pintauro, N., "Soluble Coffee Manufacturing Processes," Noyes Development Corp., 1969, pp. 72–73, 116–129.
Ukers, W., *Tea and Coffee Trade Journal*, 1935, pp. 292–296.
Union Carbide Corporation, *Carbowax® Polyethylene Glycols and Methoxypolyethylene Glycols*, 07/96.
Union Carbide Corporation, Material Safety Data Sheet *Carbowax Sentry Polyethylene Glycol 8000 Flake, Powder or Molten NF, FCC Grade*, Jan. 12, 1995.

*Primary Examiner*—Anthony J. Weier
(74) *Attorney, Agent, or Firm*—Christensen O'Connor Johnson Kindness PLLC

(57) ABSTRACT

A process for producing acid reduced coffee beans. An aqueous solution including potassium hydroxide and polyethylene glycol is applied to whole bean coffee immediately after roasting. The water from the solution dries, leaving a coating that reduces oxidation and flavor loss from the whole bean coffee, and which reduces the acidity of coffee beverages subsequently brewed from the beans. In an alternate embodiment, the potassium hydroxide and polyethylene glycol are applied in separate steps.

14 Claims, 2 Drawing Sheets

ACID REDUCED WHOLE BEAN COFFEE AND PROCESS

CROSS-REFERENCE TO RELATED APPLICATION

The present application claims the benefit of U.S. provisional patent application Serial No. 60/156,622, filed Sep. 27, 1999, and is also a continuation-in-part of copending U.S. patent application Ser. No. 09/089,927, filed Jun. 3, 1998, now U.S. Pat No. 6,045,843, which is a continuation-in-part of U.S. patent application Ser. No. 08/772,168, filed Dec. 20, 1996, now U.S. Pat. No. 6,066,342, which is a continuation-in-part of U.S. patent application Ser. No. 08/577,147, filed Dec. 22, 1995, now U.S. Pat. No. 5,853,787, priority of the filing date of which is hereby claimed under 35 U.S.C. §120.

FIELD OF THE INVENTION

The present invention relates generally to an antacid composition for neutralizing excess stomach acid, and more specifically to an antacid composition that includes potassium hydroxide.

BACKGROUND OF THE INVENTION

The oral administration or consumption of acid neutralizing agents (antacids) to treat excess gastric acid and relieve its associated discomfort is well known. Generally, antacid compositions include, as active ingredients, one or more alkaline substances in combination with other inactive ingredients. The antacid composition's alkaline components effect gastric acid neutralization while the inactive ingredients serve either as a carrier to facilitate administration or to enhance the composition's appeal, palatability, dispensability, and ease of manufacture.

Ideally, an antacid provides rapid and long-lasting relief from the discomfort associated with excess stomach acid. In addition, an effective antacid provides rapid and long-lasting relief in a convenient administrable form and dosage.

A variety of alkaline substances have been previously employed as active ingredients in antacid formulations. For example, U.S. Pat. No. 4,801,608 to Bos et al. describes a bismuth containing composition that is effective for the treatment of peptic ulcers. Aluminum hydroxide containing antacid compositions have been described in U.S. Pat. Nos. 4,514,389 and 4,576,819 to Miyata et al. and U.S. Pat. No. 5,461,082 to Machimura et al. Carbonates and bicarbonates of sodium, potassium, and calcium have also been employed as acid neutralizing agents in various antacid formulations. See, for example, U.S. Pat. No. 4,327,076 to Puglia et al. (calcium carbonate); U.S. Pat. Nos. 4,857,332; 4,904,473, and 4,976,963 to Schricker et al. (calcium carbonate and sodium bicarbonate); and U.S. Pat. No. 5,498,426 to Wilson et al. (calcium carbonate and potassium bicarbonate).

Acid neutralizing agents have also been combined with various carriers in the formulation of antacid compositions. For example, U.S. Pat. No. 2,477,080 to Necheles et al. relates to an antacid preparation composed of an acid neutralizing agent such as magnesium oxide, calcium carbonate, or sodium bicarbonate, and a carrier, carboxymethyl cellulose, to increase the residency time of the acid neutralizing agent in the stomach and thereby afford long-lasting antacid activity.

Although the active ingredients of commercially available, over-the-counter antacid compositions vary, many of these antacids include alkaline earth (e.g., calcium and magnesium) carbonates and hydroxides. More specifically, calcium carbonate is a primary acid neutralizing agent common to many commercially available antacid formulations (e.g., ROLAIDS, TUMS, MYLANTA, MEDACID). In fact, calcium carbonate is the sole active ingredient in TUMS. To counteract its constipative effect, calcium carbonate is often used in combination with magnesium salts such as magnesium carbonate, magnesium hydroxide, and magnesium oxide, in antacid compositions (e.g., ROLAIDS, MYLANTA, MEDACID).

Generally, antacid compositions containing weak acid neutralizing agents such as calcium carbonate and aluminum hydroxide are slow acting and consequently do not provide rapid relief to the discomfort associated with excess stomach acid. More rapid acting antacids may include magnesium hydroxide, a stronger acid neutralizing agent. Although primarily incorporated into calcium carbonate containing antacids for its anticonstipative effect, magnesium hydroxide is also known for its antacid activity.

Other more highly alkaline substances, such as sodium and potassium hydroxide, exhibit a still stronger neutralizing effect. However, despite their great ability to neutralize acid, the sodium and potassium hydroxide have not been used as active ingredients in antacid compositions for human consumption. This is apparently due to the corrosive nature of these strong bases. Potassium hydroxide, for example, can be extremely corrosive to all tissues, and ingestion of significant quantities in some circumstances can produce pain in the throat and epigastrium, hematemesis, collapse, and stricture of the esophagus. In extreme cases, ingestion may be fatal. Sodium hydroxide is similarly caustic and toxic.

Although not specifically incorporated as an active antacid ingredient, potassium hydroxide is included among the ingredients as a potassium source in a ruminant feed composition described in U.S. Pat. No. 4,976,963 to Schricker et al. and in the colloidal antacid described in U.S. Pat. No. 4,801,608 to Bos et al. Schricker's feed pellet includes an antacid component (i.e., a mixture of a sodium or magnesium antacid) and an electrolyte component to provide potassium, sodium, and chlorine (i.e., a potassium, sodium, or chlorine-containing electrolyte) in the diet. Potassium hydroxide is described in the patent as a suitable potassium source. The colloidal bismuth antacid composition of Bos optionally includes potassium hydroxide to maintain the pH of the colloidal suspension in a range so as prevent the precipitation of bismuth from the colloid.

In at least one instance, potassium hydroxide has been utilized as an acid neutralizing agent in a feed additive for nonhuman consumption. U.S. Pat. No. 5,314,852 to Klatte describes a potassium hydroxide-impregnated zeolite that is useful as a feed supplement to ruminant animals (e.g., cows) to provide buffering in several digestive organs. However, Klatte cautions that the activity rate may be too high for some animal feed applications and that potassium hydroxide is much too caustic to feed alone to such animals.

Accordingly, despite the great number of antacid compositions, some of which are noted above, there remains a need for a rapid acting and long-lasting antacid composition that may be orally administered in a safe and effective amount to an individual suffering from the discomfort associated with excess stomach acid. The present invention seeks to fulfill these needs and provides further related advantages.

The consumption of acidic food and beverages often results in physical discomfort in the form of indigestion and heartburn, among other discomforts. Acidic beverages including coffees and teas are particularly troublesome because of their widespread consumption and elevated acid concentrations.

Coffee is a morning ritual for over 125 million Americans, with the average coffee drinker consuming three cups of coffee per day. However, drinking coffee does not affect all people in the same way. While some are able to drink an entire pot of coffee without experiencing any adverse effects, others may experience indigestion and discomfort. In addition to discomfort, potential health risks associated with excessive coffee consumption in general, and with caffeine consumption in particular, have been theorized. At least one study has linked coffee consumption to osteoporosis. Pregnant mothers are often cautioned to limit their intake of coffee as a precaution to ensure the health and safety of their unborn children. It is not well understood what the effects of coffee acids may be on the health of the general population, but at a minimum acidic coffee causes discomfort for many people with digestive tract disorders, such as acid reflux or ulcers.

Coffee is a complex composition derived from the brewing of roasted and ground coffee beans. The constituents of coffee beans include caffeine (1–2%), coffee oil (10–15%), sucrose and other sugars (about 8%), proteins (about 11%), ash (about 5%), and chlorogenic and caffeic acids (about 6%). Other constituents include cellulose, hemicelluloses, trigonelline, carbohydrates, volatile oils, and other acids. The composition of a particular coffee is variable and depends upon such factors as the type of bean, where the coffee is grown and harvested, and how the beans are processed. It is the individual constituents of a coffee that contribute to its natural aroma, flavor, and appeal.

Many different acidic constituents are present in coffee. Coffee's acids include malic acid, tannic acid, maleic acid, oleic acid, oxalic acid, caffeic acid, and chlorogenic acid, among others. These acidic constituents are responsible for the overall acidity of coffee and the discomfort that occasionally arises from the ingestion of this acidic beverage. Furthermore, coffee contains caffeine, which, upon ingestion, causes the gastric secretion of acids. Accordingly, coffee drinking not only results in the ingestion of an acidic beverage, but also stimulates the production of additional acids.

Commonly, the coffee drinker's solution to discomfort arising from coffee's acidity is to either reduce the number of cups of coffee consumed each day, avoid drinking coffee entirely, or alternatively, dilute the coffee, or accompany coffee drinking, with dairy products such as milk or cream. Unfortunately, the use of dairy products as a solution to the problem of coffee acidity is not universal. Many people, including some coffee drinkers, suffer from lactose intolerance and have difficulty in digesting milk sugars. For these individuals, the problem of coffee acidity is not solved by the addition of milk products to coffee.

The problem of reducing the acidity of certain foods and beverages has been previously addressed. For example, a process for decreasing the malic acid content in wines involving the treatment of wine with a composition including calcium carbonate, potassium bicarbonate, and calcium tartrate has been described. U.S. Pat. No. 4,461,778. A malolactic fermentation process that provides a coffee product having reduced malic acid content has also been described. U.S. Pat. Nos. 4,976,983 and 5,147,666. A common practice in red wine production involves treating the wine with gelatin, which selectively neutralizes tannic acid.

Alkaline treatments have been used in the production of coffee products. For example, in the preparation of instant coffee, coffee extracts have been treated with alkaline materials including ammonia, alkali metal and alkaline earth metal hydroxides, carbonates, and bicarbonates to improve the yield of soluble solids. U.S. Pat. No. 3,644,122. Similarly, alkaline molecular sieves have been employed in a process for improving yield in secondary coffee extracts in the production of soluble coffee. U.S. Pat. No. 5,229,155. A process for preparing a better tasting coffee involving an intermediate step of treating partially roasted coffee beans with an aqueous alkaline solution of a foodgrade base, such as sodium hydroxide, ammonium hydroxide, calcium hydroxide, or ammonium bicarbonate, prior to final roasting is also known. U.S. Pat. No. 4,986,271.

In some cultures, roasted and ground coffee is customarily brewed together with egg and eggshells. Presumably, this treatment reduces the acidity of the resulting brewed coffee. W. Ukers, *Tea and Coffee Trade Journal,* 1935. To bring out the full flavor and strength of coffee, a coffee composition comprising a roasted coffee bean coated with alkali, such as borax or bicarbonate of soda, has been disclosed. U.S. Pat. No. 312,516. Today, borax is considered unsafe for human consumption, and the ingestion of sodium is often considered inadvisable for individuals on low sodium diets. An alkaline substance, lithium carbonate, has been utilized as a preserving agent for roasted and ground coffee. U.S. Pat. No. 2,419,031. A process for making coffee more digestible by raising its pH by the addition of an acid binding substance is also known. U.S. Pat. No. 2,036,345. In this process, the acid binding substance is a basic or alkaline material non-injurious to health and includes alkaline earth metal oxides, hydroxides, carbonates, and bicarbonates as well as alkali metal carbonates, bicarbonates, and alkaline phosphates. In a preferred embodiment, the acid binding substance includes trisodium phosphate and potassium bromide. Today, neither of these two ingredients is considered by the Food and Drug Administration to be Generally Regarded As Safe (GRAS).

Accordingly, despite the methods and compositions for treating coffee mentioned above, there remains a need in the art for a composition and method for reducing the acidity of foods and beverages, such as coffee, that are safe for a broad segment of the population, economical, and easy to use. The present invention addresses these needs and provides further related advantages.

Many individuals also suffer digestive problems after drinking milk or consuming other uncultured dairy products, due to the inability to digest lactose, e.g., milk sugar. Such lactose intolerant individuals typically either forego dairy products, thus missing the calcium and protein advantages thereof, or consume lactose reduced milk and dairy products. Conventional lactose reduced milk has been treated with an enzyme that partially hydrolyzes the lactose. Enzyme treatment adds a time consuming step and expense to the milk production process.

SUMMARY OF THE INVENTION

The present invention relates generally to antacid and acid-neutralizing compositions and methods of their use in neutralizing acids. In one aspect of the present invention, an antacid composition that is useful in neutralizing excess stomach acid and relieving discomfort in persons suffering from acid indigestion is disclosed. In another aspect, the present invention discloses an acid-neutralizing composition that is useful in reducing the acidity of acidic foods and beverages.

In one aspect, the invention relates to an antacid composition comprising an alkaline earth metal carbonate, preferably calcium carbonate; an alkali metal hydroxide, preferably potassium hydroxide; and an alkaline earth metal hydroxide, preferably magnesium hydroxide. In a preferred embodiment, calcium carbonate is present in the composition in an amount ranging from 20 to 90 percent by weight of the total composition, potassium hydroxide is present in an amount ranging from 0.5 to 5 percent by weight of the total composition, and magnesium hydroxide is present in an amount ranging from 0.1 to 10 percent by weight of the total composition. The antacid formulation may additionally include potassium chloride, an excipient, and a flavoring agent. Suitable excipients include granulating agents such as microcrystalline cellulose, croscarmellose sodium NF, and silicon dioxide. Suitable flavoring agents include spearmint flavorant, sucrose, fructose, and NutraSweet®. In a particularly preferred embodiment, the antacid composition includes calcium carbonate, potassium hydroxide, magnesium hydroxide, microcrystalline cellulose, croscarmellose sodium NF, silicon dioxide, a spearmint flavorant, and sucrose.

In another aspect, the present invention discloses a method for neutralizing excess stomach acids. In the method, a safe and effective amount of an antacid composition including calcium carbonate, potassium hydroxide, and magnesium hydroxide is orally administered to a human in need thereof.

The present invention additionally relates to methods of reducing the acidity of acidic foods and acidic beverages through the use of an acid-neutralizing composition. More specifically, the present invention relates to methods and compositions for brewing coffee having reduced acidity. The availability of methods and compositions of this invention to the general public enables the consumer, for the first time, to adjust the acidity of any food or beverage to suit the consumer's taste. Previous methods were available only to manufacturers.

In an aspect of the invention, methods of brewing coffee having reduced acidity are disclosed. In the method, an acid-neutralizing composition is added to a coffee product in an amount sufficient to produce a brewed coffee having a pH of from about 5.7 to about 6.1. In an embodiment, the method includes adding an acid-neutralizing composition to whole coffee beans. In another embodiment, the method includes the addition of an acid-neutralizing composition to ground coffee beans. In yet another embodiment, the method includes the addition of an acid-neutralizing composition to a brewed coffee beverage. In still another embodiment, the method includes brewing coffee utilizing a coffee filter impregnated with an acid-neutralizing composition.

In another aspect, the present invention discloses an acid-neutralizing composition. In general, the acid-neutralizing composition comprises alkaline (i.e., basic) substances and affords both rapid and long-lasting antacid activity. Suitable alkaline substances of the present invention include alkaline earth metal carbonates, alkali and alkaline earth metal hydroxides, and aluminum hydroxide. In a preferred embodiment, the alkaline substances include calcium carbonate, potassium hydroxide, and magnesium hydroxide. The acid-neutralizing composition may additionally include potassium chloride, gelatin, bacteria and fungi retarders, vitamin D, and excipients. Suitable excipients include granulating agents, dispersing agents, instant coffee, and nondairy creamers. In a particularly preferred embodiment, the acid-neutralizing composition includes calcium carbonate, potassium hydroxide, magnesium hydroxide, potassium chloride, vitamin D, and instant coffee.

In another embodiment, the present invention includes a coffee product comprised of whole coffee beans and an acid-neutralizing composition. In a further embodiment, the invention includes a coffee product comprised of ground coffee beans and an acid-neutralizing composition.

In a further aspect of the present invention, an acid reduced coffee bean product, and process for producing the same, is provided. In a preferred embodiment, whole coffee beans are roasted, and then coated with a coating including an alkaline agent and a coating agent. Preferably, the alkaline agent includes potassium hydroxide, and the coating agent includes polyethylene glycol. The potassium hydroxide and polyethylene glycol are preferably applied to the beans as an aqueous solution that is sprayed onto the beans after roasting, and preferably applied to the beans while still hot from roasting. The coating serves to reduce the acidity of coffee subsequently brewed from the beans, while also providing protection against oxidation of the coffee beans and preserving coffee bean flavor. The alkaline agent and the coating agent can be applied separately or together.

In a further aspect of the present invention, a method of reducing lactose in milk and other uncultured dairy products is provided, as well as lactose-reduced milk and dairy products produced thereby. A composition including an alkali metal hydroxide and an alkaline earth metal hydroxide is introduced to milk prior to consumption. A lactose-reduced milk product is produced thereby, without detrimentally effecting the natural taste and flavor of the milk. Preferably the lactose-reducing composition of the present invention includes potassium hydroxide and magnesium hydroxide. The composition may also include an alkaline earth metal carbonate, such as calcium carbonate. In the preferred embodiment, calcium carbonate is included in an amount ranging from 20 to 90% by weight of the total composition, potassium hydroxide at 0.5 to 5% by weight of the total composition, and magnesium hydroxide at from 0.1 to 10% by weight of the composition. The lactose-reducing composition is suitably added at a range of 0.05 to 0.3% by weight of the milk.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
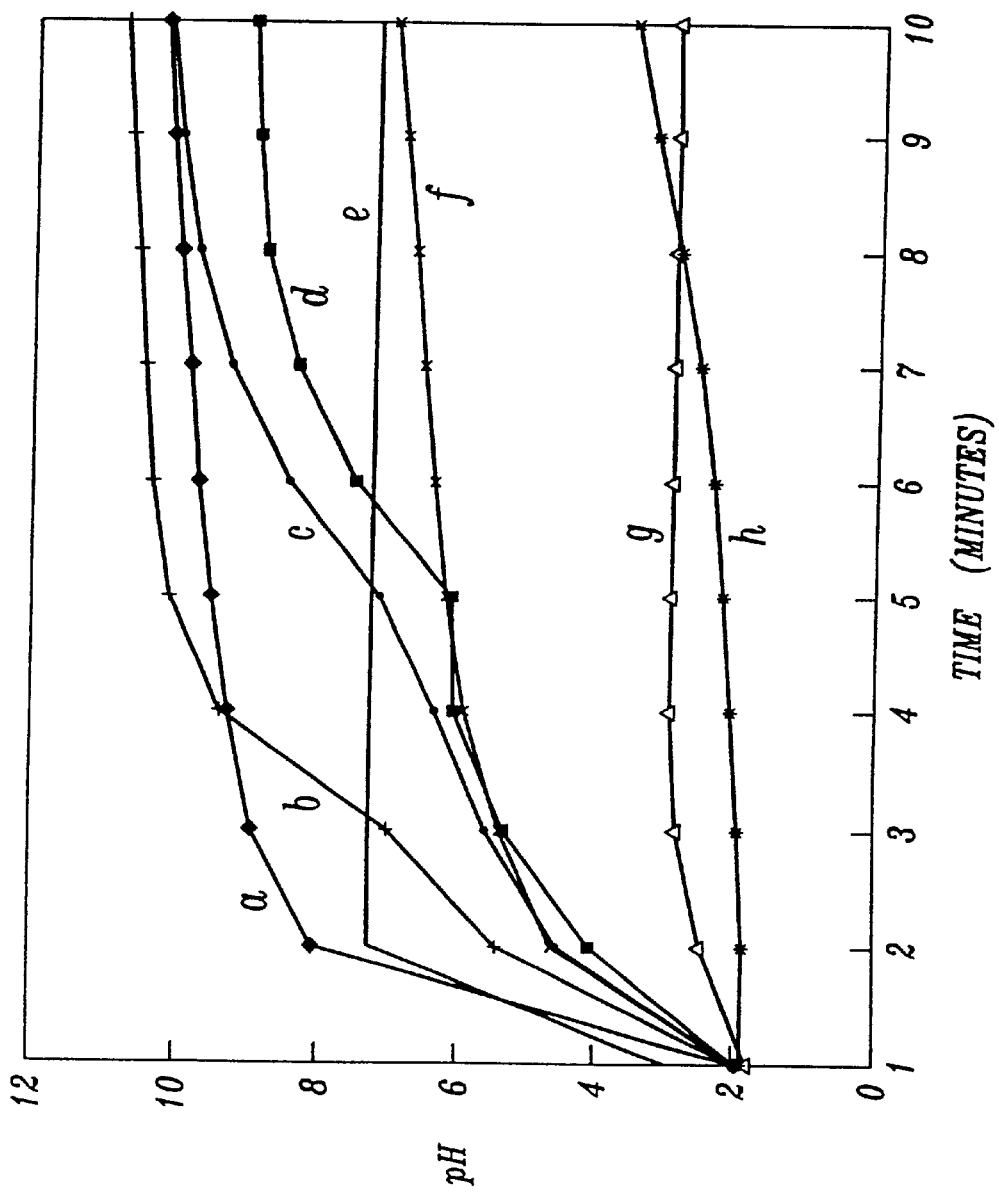
FIG. 1 is a graph comparing the change in pH over time of acidic solutions treated with a representative antacid composition of the present invention (a) and several commercially available antacids: MEDACID (b), ROLAIDS (c), MYLANTA (d), PRELIEF (e), TUMS (f), GAVISCON (g), and MAALOX (h)

The present invention relates generally to antacid and acid-neutralizing compositions and methods for their use in neutralizing acid. As used herein, the terms "antacid" and "acid-neutralizing" are used interchangeably and refer to compositions that, when added to an acidic environment, reduce the acidity of the environment. In one aspect, the present invention generally relates to methods and compositions useful in reducing the acidity of acidic foods and beverages. In this aspect, the present invention is directed to methods and compositions for brewing coffee having reduced acidity. In another aspect, the invention relates generally to methods and compositions useful in neutralizing excess stomach acid and relieving discomfort in humans suffering from acid indigestion.

In one aspect of the invention, methods of brewing coffee having reduced acidity is disclosed. In these methods, the acidity of coffee is reduced through the use of an acid-neutralizing composition. The methods of the present invention provide a brewed coffee having a pH of from about 5.7 to about 6.1. The methods are applicable to brewing methods that utilize either whole or ground coffee beans. The present invention also includes a method for reducing the acidity of a brewed coffee beverage. As noted above, the methods are also applicable to reducing the acidity of liquid foods.

In another aspect of the present invention, an acid-neutralizing composition is disclosed. The acid-neutralizing composition comprises alkaline (i.e., basic) substances and affords both rapid and long-lasting antacid activity. As used herein, the term "antacid activity" refers to the ability of a substance to neutralize and/or to buffer an acid. Neutralization refers to a acid-base reaction by which an acid is made neutral. Neutralization does not necessarily mean attaining neutral pH (i.e., pH 7), rather, neutralization refers to the equivalence point for a particular acid-base reaction and will depend upon the respective strengths of the particular acid and base, their relative concentrations, and the buffering properties of the solution containing the acid and base. A buffer is a solution containing salts of weak acids that is capable of neutralizing both acids and bases and acts to maintain the pH of a solution. In other words, a buffered solution contains both a weak acid (e.g., acetic acid) and its conjugate weak base (e.g., sodium acetate) and its pH changes only slightly upon the addition of acid or base. The weak acid acts as a buffer when base is added to the solution, and the weak base acts as a buffer when acid is added to the solution. In the context of the present invention, the addition of an acid-neutralizing composition to an acidic food or beverage results in the neutralization of acids, thereby reducing the acidity of the food or beverage. At the same time, the food or beverage becomes buffered, that is, the pH of the food or beverage may be maintained, within limits, upon the addition of more acid.

Alkaline substances having long-lasting antacid activity include alkali and alkaline earth metal carbonates. For example, the pharmaceutical use of calcium carbonate as an effective stomach antacid is well known. The rapid antacid effect of stronger alkaline substances such as alkali and alkaline earth metal hydroxides is also known. Commonly used alkali and alkaline earth metal hydroxides include lithium, sodium, potassium, calcium, and magnesium hydroxides.

As noted above, the acid-neutralizing composition of this invention includes a combination of alkaline substances having both rapid and long-lasting antacid activity. As such, the composition of the present invention is particularly well suited for reducing the acidity of caffeinated beverages such as coffee. The rapid acting alkaline substances (e.g., potassium hydroxide and magnesium hydroxide) of the composition effectively reduce the acidity of the beverage itself, while the long-lasting alkaline substances (e.g., calcium carbonate) counteract and neutralize acidic gastric secretions stimulated by the ingestion of caffeine.

The alkaline substances of the present invention include alkaline earth metal carbonates, alkali and alkaline earth metal hydroxides, and aluminum hydroxide. More specifically, alkaline earth metal carbonates include calcium and magnesium carbonates, and alkali and alkaline earth metal hydroxides include potassium and magnesium hydroxides. In addition to alkaline substances, the acid-neutralizing composition includes potassium chloride. In a preferred embodiment, the acid-neutralizing composition comprises calcium carbonate, potassium hydroxide, magnesium hydroxide, and potassium chloride. In suitable embodiments, calcium carbonate is present in the composition in an amount ranging from about 60% to about 90% by weight of the total composition, potassium hydroxide is present in an amount ranging from about 5% to about 15% by weight of the total composition; magnesium hydroxide is present in an amount ranging from about 0.1% to about 10% by weight of the total composition; and potassium chloride is present in an amount ranging from about 1% to about 5% by weight of the total composition.

In a preferred embodiment, calcium carbonate is present in the composition in an amount ranging from about 65% to about 80% by weight of the total composition; potassium hydroxide is present in an amount ranging from about 6% to about 8% by weight of the total composition, magnesium hydroxide is present in an amount ranging from about 0.5% to about 2% by weight of the total composition; and potassium chloride is present in an amount ranging from about 2% to about 3% by weight of the total composition.

Of these acid neutralizing compounds, potassium hydroxide is the most active neutralizer, effective at neutralizing maleic, oxalic, and to some extent, chlorogenic acids. The remaining compounds of the preferred composition are less active. Magnesium hydroxide supplements the neutralizing effect of the potassium hydroxide, and is the secondmost active neutralizer. Calcium carbonate acts as a weak neutralizer, but also serves as a diluent to provide a convenient application quantity of the composition, and as a calcium source. The potassium chloride is included primarily for flavor, providing a salty flavor to substitute for the acid flavor of untreated coffee. The combination of these ingredients of the composition provides a highly effective acid neutralizer that does not detrimentally alter the flavor of treated brewed coffee.

The alkaline substances noted above are the active ingredients primarily responsible in reducing the acidity of an acidic food or beverage. In addition to their antacid activity, the alkaline substances provide additional effects beneficial to health and nutrition. For example, magnesium hydroxide present in the composition has the effect of counteracting the constipative effect that often accompanies the ingestion of calcium carbonate. Furthermore, from a dietary standpoint, the alkaline substances also provide calcium, potassium, and magnesium, minerals for which the Food and Drug Administration has proposed minimum daily requirements.

In another embodiment of the acid-neutralizing composition, in addition to the alkaline substances noted above, the composition further includes foodgrade gelatin as an active ingredient. In a preferred embodiment, the gelatin is foodgrade, type B gelatin. Generally, for the acid-neutralizing compositions of the invention that include gelatin, gelatin is present in an amount up to about 3% by weight of the total composition. The gelatin is useful in the composition for neutralizing tannic acid, an acid present in the fruit of many plants, and one of the acids present in coffee. In a preferred embodiment, acid-neutralizing compositions that include gelatin also include a bacteria and/or fungi retarder. Suitable bacteria and/or fungi retarders include any such retarder that is effective in preventing the growth of bacteria and/or fungi in the composition. The bacteria and/or fungi retarder is present in an amount to effectively prevent the growth of bacteria and/or fungi, typically in an amount ranging from about 0.01% to about 0.2% by weight of the total composition. Preferred bacteria and/or fungi retarders include methyl paraben and propyl paraben. In one preferred embodiment, the acid-neutralizing composition includes methyl paraben in an amount ranging from about 0.01% to about 0.03% by weight of the total composition and propyl paraben in an amount ranging from about 0.07% to about 0.09% by weight of the total composition.

In addition to the alkaline substances mentioned above, the acid-neutralizing composition of this invention may include other ingredients. Thus, in another embodiment, the acid-neutralizing composition includes vitamin D. Preferably, vitamin D is vitamin $D_3$ and is present in the composition in an amount ranging from about 0.1% to about 0.5% by weight of the total composition. Addition of an amount of the acid-neutralizing composition sufficient to produce a cup of coffee having a pH of from about 5.7 to about 6.1 provides a cup of coffee having about 100 IU (international units) of vitamin D. While vitamin D is not an alkaline substance useful in reducing acidity, vitamin D is active in calcium uptake. Accordingly, because of the beneficial aspects of dietary calcium (i.e., recommended daily allowance of 800 to 1500 milligrams) and because the composition of this invention includes calcium as a primary ingredient, the addition of vitamin D to the composition provides further nutritional and health benefits.

The composition of this invention may also include an excipient. As used herein, the term "excipient" refers to an inert substance that forms a vehicle for the active ingredients of the composition. In the context of the present invention, suitable excipients include those that permit the effective and efficient delivery of the alkaline substances and other ingredients present in the composition of this invention, and include granulating and dispersing agents. For example, the acid-neutralizing composition may be formulated as a free-flowing solid such as a powder or granule using a granulating agent. A preferred granulating agent useful in rendering the composition a free-flowing solid is microcrystalline cellulose. Another preferred granulating agent is fumed silicon dioxide available from commercial sources (e.g., Cabot Corp., Tuscola, Ill.) and useful in controlling granule density. Furthermore, in one embodiment, the composition as a free-flowing solid is delivered to an acidic beverage where it is dispersed into solution. To assist in dispersion of the composition into solution, the composition may include a dispersing agent. A preferred dispersing agent useful for smooth dispersal of the composition in solution is carboxymethyl cellulose. In another embodiment, the excipient is soluble coffee (also known as instant coffee). In yet another embodiment, the excipient is a nondairy creamer.

In general, an excipient is present in the composition in an amount ranging from about 5% to about 30% by weight of the total composition. In a preferred embodiment, the acid-neutralizing composition includes microcrystalline cellulose in an amount from about 2% to about 10% by weight of the total composition, carboxymethyl cellulose sodium in an amount from about 2% to about 20% by weight of the total composition, and instant coffee in an amount from about 0.1% to about 0.5% by weight of the total composition. Instant coffee is suitably added to the composition to provide an appealing coffee color. Instant coffee is not required for the composition's efficacy in reducing acidity.

The acid-neutralizing composition may also be formulated as a liquid solution. When the composition is formulated as a liquid, the excipient may be water including sterile and/or distilled water.

As described above, the acid-neutralizing composition includes alkaline substances (i.e., preferably calcium carbonate, magnesium carbonate, potassium hydroxide, magnesium hydroxide, and gelatin) that are active in reducing the acidity of an acidic food or beverage; other ingredients (i.e., vitamin D) that offer additional health and nutritional benefits; and inert ingredients (i.e., potassium chloride, bacteria and/or fungi retarders, and excipients) that provide practical effectiveness relating to composition stability and formulation. All of these ingredients are Generally Regarded As Safe (GRAS) for use by the Food and Drug Administration.

Representative acid-neutralizing compositions of the present invention are described in Examples 1–3. Example 3 describes a representative acid-neutralizing composition of this invention that includes gelatin.

The acid-neutralizing composition of the present invention may be formulated in a variety of ways. As noted above, the composition may be formulated as a free-flowing solid, such as a powder or granule. The composition of the present invention may be granulated in any one of many granulation techniques known in the art. One suitable method involves the mixing of all dry components of the composition in water to form partially agglomerated clumps, followed by drying, chopping, and shifting to produce the desired granules. Other granulation methods well known to those of ordinary skill in the art include: spray drying; extrusion and chopping; grinding; the use of a fluid bed; and high shear granulation. The formulation of an acid-neutralizing composition of this invention as a free-flowing granule is described in Example 1. In addition to flowing solids, the composition may also be formulated as a pill, tablet, or capsule. The composition may also be formulated as a liquid, such as an aqueous solution, slurry, emulsion, or syrup.

The present invention also provides coffee products. In one embodiment, this invention provides a coffee product comprising whole coffee beans and an acid-neutralizing composition. In another embodiment, a coffee product comprising ground coffee beans and an acid-neutralizing composition is provided. In these coffee products, the acid-neutralizing composition is present in an amount sufficient to produce a brewed coffee having a pH of from about pH 5.7 to about 6.1. Typically, about 10 to 20 grams of the acid-neutralizing composition added to one kilogram of coffee is sufficient to produce a brewed coffee having such reduced acidity.

As noted above, one aspect of the present invention provides methods for reducing the acidity of an acidic food or beverage by the addition of an acid-neutralizing composition. In the context of this invention, acidic foods include liquid foods, such as tomato products including tomato paste, vinegar-containing products such as salad dressing, and cranberry products including cranberry sauce. Acidic beverages include any beverage having a pH less than about 4, including coffee beverages, tea beverages, and fruit juice beverages such as tomato juice and cranberry juice beverages, and citrus fruit beverages including orange and grapefruit juice beverages.

While the pH of coffee beverages will depend on many factors, including the type of coffee bean, strength of the brew, and brewing conditions, the pH of most coffees falls within the range of from pH 4.8 to about pH 5.7. The present invention provides methods for reducing the acidity (i.e., increasing the pH) of coffee beverages. Preferably, the methods of the invention provide a coffee beverage having a pH in the range from about pH 5.7 to about pH 6.1.

Generally, the present invention provides a method of brewing coffee having reduced acidity that includes adding an acid-neutralizing composition to a coffee product in an amount sufficient to produce a brewed coffee having a pH of from about pH 5.7 to about pH 6.1. In the context of the present invention, a coffee product includes whole coffee beans, ground coffee beans, and brewed coffee.

Other known processes for the deacidification of coffee include alkaline treatment of either green or semiroasted beans at elevated temperature (e.g., 375° to 425° F.) for prolonged periods of time (e.g., 10 to 25 minutes depending upon the type of bean, its moisture content, and the roast desired). Typically, under these conditions, the deacidification is accompanied by saponification of coffee oils resulting in alteration of the coffee's flavor and aroma. To a large extent, the oils of the coffee impart its flavor and aroma.

In contrast, as described below, the methods of the present invention utilize an acid-neutralizing composition under conditions that preserve the flavor and aroma of the coffee. In the present methods, a coffee product is combined with the acid-neutralizing composition at relatively low temperature (e.g., about 220° F., the boiling point of water) for a short period of time (e.g., about 3 to 5 minutes, the time required to prepare a brewed coffee). Accordingly, the methods of this invention result in a coffee having reduced acidity without compromising the flavor, aroma, and taste integrity of the resulting brewed coffee.

In one embodiment, the present invention provides a method of brewing coffee having reduced acidity. In the method, an acid-neutralizing composition, as described above, is added to whole coffee beans to provide a whole coffee bean and acid-neutralizing composition mixture. The whole coffee bean and acid-neutralizing composition mixture is then subjected to grinding to provide a ground coffee bean and acid-neutralizing composition mixture. Finally, the ground coffee bean and an acid-neutralizing composition mixture are brewed with water to provide a brewed coffee having reduced acidity.

In this method, the reduction of acidity of a coffee beverage depends upon the quantity of the acid-neutralizing composition added to the whole coffee beans. In addition, the amount of an acid-neutralizing composition added to the whole beans will depend upon many factors including the nature and type of coffee bean. Generally, to provide a coffee beverage having reduced acidity and a pH in the range from about 5.7 to about 6.1, approximately 15 grams of the acid-neutralizing composition of this invention are added to approximately one kilogram of whole coffee beans.

In another embodiment, the present invention provides a method of brewing coffee having reduced acidity where an acid-neutralizing composition is added to ground coffee beans. In this method, the addition of an acid-neutralizing composition to ground coffee beans provides a ground coffee bean and acid-neutralizing composition mixture, which is then brewed with water to provide a brewed coffee having reduced acidity.

Similar to the above method, the reduction of acidity of a coffee beverage depends upon the quantity of the acid-neutralizing composition added to the ground coffee beans, which in turn depends upon factors including the nature and type of coffee bean. Generally, to provide a coffee beverage having reduced acidity and a pH in the range from about 5.7 to about 6.1, approximately 15 grams of the acid-neutralizing composition of this invention are added to approximately one kilogram of ground coffee beans.

In yet another embodiment, this invention provides a method of preparing a coffee beverage having reduced acidity where an acid-neutralizing composition is added directly to a brewed coffee beverage. In this method, an acid-neutralizing composition is added directly to a brewed coffee, such as a cup or pot of coffee, such that the pH of the resulting brewed coffee has a pH in the range from about pH 5.7 to about pH 6.1. As noted above, the quantity of acid-neutralizing composition to effect the reduction of acidity to this preferred pH range will depend upon the acidity of a brewed coffee beverage. In general, about 100 mg of acid-neutralizing composition will increase the pH of an 8-ounce cup of coffee from about pH 5 to about pH 6. Accordingly, approximately 1.2 grams of the composition would similarly reduce the acidity of a twelve-cup pot of coffee to a pH range of about pH 5 to about pH 6.

All of the methods noted above offer the advantage that the coffee brewer may reduce the acidity of her coffee beverage to suit her own taste. Accordingly, the coffee brewer may add more or less of the acid-neutralizing composition as desired.

In still another embodiment, a method for brewing coffee having reduced acidity is provided where a coffee filter impregnated or coated, such as by silk-screening, with an acid-neutralizing composition is utilized in brewing the coffee beverage. In this method, ground coffee beans are placed in a coffee filter impregnated or coated with an acid-neutralizing composition, and the coffee is then brewed in the usual manner. The acid-neutralizing composition is present in the filter in an amount sufficient to produce a brewed coffee having a pH from about pH 5.7 to about 6.1.

In addition to coating or impregnating coffee filters, other paper constructs that come into contact with brewed coffee or other acidic beverages or foods can likewise be treated with the acid-neutralizing composition of the present invention. Thus, the acid-neutralizing composition can be applied to the interior of paper cups for use with coffee, tea, orange juice, etc., or to the interior of paper bowls or plates for acidic foods. The composition is applied, such as by impregnation or silk-screening, in an amount sufficient to reduce the food or beverage acidity by a predetermined amount. The coating can be applied in a pattern of small "dots" or deposits of acid-reducing composition, or can be applied in a uniform layer.

The methods and compositions of the present invention provide brewed coffee having reduced acidity while at the same time maintaining the taste integrity of the coffee. Taste tests have been conducted and have demonstrated that no detrimental effect to coffee flavor occurs in the practice of the methods of the present invention. In fact, in several instances, coffees produced by these methods were rated as having a better taste than plain coffee. Some taste tests and their results are described in Example 4.

As noted above, in another aspect, the invention also relates to compositions and methods useful in neutralizing excess stomach acid in humans. Like the acid-neutralizing composition noted above, the antacid composition also includes alkaline substances that afford both rapid and long-lasting antacid activity. The antacid composition includes an alkaline earth metal carbonate, preferably calcium carbonate; an alkali metal hydroxide, preferably potassium hydroxide; and an alkaline earth metal hydroxide, preferably magnesium hydroxide. In preferred embodiments, calcium carbonate is present in the composition in an amount ranging from about 20 to 90% by weight of the total composition; potassium hydroxide is present in the composition in an amount ranging from about 0.5 to about 10% by weight of the total composition; and magnesium hydroxide is present in the composition in an amount ranging from about 0.1 to about 10% by weight of the total composition.

In a more preferred embodiment, calcium carbonate is present in the composition in an amount ranging from about 25 to about 45% by weight of the total composition; potassium hydroxide is present in the composition in an amount ranging from about 1 to about 10% by weight of the total composition; and magnesium hydroxide is present in the composition in an amount ranging from about 1 to about 5% by weight of the total composition.

Of these ingredients, potassium hydroxide is the strongest and most rapid acting acid neutralizer. Magnesium hydroxide is intermediate in its neutralizing activity and supplements the antacid activity of potassium hydroxide, and calcium carbonate acts as a weak acid neutralizer and imparts long-lasting antacid activity to the composition.

In addition to the alkaline substances noted above, the antacid composition of this invention may include other ingredients. Thus, in another embodiment, the antacid composition includes potassium chloride as mouthfeel and taste enhancer. Preferably, potassium chloride is present in the composition in an amount ranging from about 0.2 to 2% by weight of the total composition.

The antacid composition of this invention may also include one or more excipients. Suitable excipients include those that enable the effective delivery of the alkaline substances and other ingredients present in the composition and include granulating and tableting agents. The granulating and tableting agents are also useful in processing the solid ingredients of the composition and formulating the antacid composition as a powder, granule, or tablet, which will dissolve or "explode" when introduced to liquid. Suitable excipients include microcrystalline cellulose, silicon dioxide, and croscarmellose sodium NF (also known as carboxyl methyl cellulose-sodium or CMC sodium). The antacid composition of the present invention may also be compounded as a liquid, specifically an aqueous suspension or solution. Excipients for liquid antacids formulated in accordance with the present invention include thickeners such as polyethylene glycol, suitably included at levels of up to 2½% by weight, and suspension agents such as silicone dioxide, suitably included at levels of up to 1% by weight, as well as microcrystalline cellulose.

In general, one or more excipients are present in the composition in an amount ranging from about 10 to about 30% by weight of the total composition. In a preferred embodiment, the antacid composition includes croscarmellose sodium NF in an amount from about 2% to about 5% by weight of the total composition, microcrystalline cellulose in an amount from about 15% to about 25% by weight of the total composition, and silicon dioxide in an amount from about 0.1% to about 2% by weight of the total composition.

The antacid composition of the invention may also include one or more flavoring agents. Suitable flavoring agents include sweetening agents and other flavorants. Suitable sweetening agents include sugars such as monosaccharides, disaccharides, and polysaccharides, for example, glucose, fructose, dextrose and sucrose; and artificial sweeteners such as saccharine, cyclamate, and dipeptide-based sweeteners such as NutraSweet®. Suitable other flavorants include mint-containing flavorants such as spearmint and peppermint flavorants as well as other similar flavorings. The amount of flavoring agent present in the antacid composition is primarily a matter of taste preference and may vary with the flavoring agent selected and with the other ingredients in the composition. The flavoring agent may be present in an amount ranging from about 2% to about 60% and preferably from about 35% to about 45% by weight of the total composition. In a preferred embodiment, the antacid composition includes a natural spearmint flavorant and sucrose.

The preferred antacid composition of this invention is an extremely low sodium-containing composition. Besides sodium impurities present in the composition's ingredients, the only source of sodium is carboxymethyl cellulose sodium, which is present in the composition in an amount from about 2% to about 5% by weight of the total composition. Under FDA standards, such a composition is considered to be sodium free. This equates to less than 0.5 mg per serving.

Used in the amounts indicated, all of the ingredients of the antacid compositions of this invention are considered by the FDA to be generally regarded as safe (GRAS). For example, the standard manufacturing practice limit for potassium hydroxide is 1200 mg/serving. When the antacid composition of this invention is used as directed, the amount of potassium hydroxide administered is significantly less than the upper limits noted above.

Representative antacid compositions of the present invention are described in Example 5. Example 6 describes the acid-neutralizing effectiveness of some representative antacid compositions of the invention and their effectiveness in acid neutralization is compared to some commercially available antacids in Examples 7 and 8.

The antacid compositions of the invention are fast acting acid neutralizers. Their rapid rate of acid neutralization was the greatest of the antacids compared (see Example 7 and FIG. 1) and may be attributed to the presence of potassium hydroxide in the composition.

Furthermore, the antacid compositions of the invention are potent acid-neutralizing compositions. On a weight basis, the amount of antacid necessary to raise the pH of an acidic solution from pH 3.0 to pH 6.0 is substantially less for the antacids of the invention than for several commercially available antacids (see Example 8 and FIG. 2).

In addition to providing antacid compositions, the present invention also provides a method for neutralizing excess stomach acid in a human. The method comprises orally administering to the human a safe and effective amount of an antacid composition as described above. As used herein, the term "safe and effective amount" refers to a quantity of the antacid composition sufficient to provide the desired antacid effect without undue adverse side effects such as toxicity, irritation, or allergic response. The specific safe and effective amount will vary with such factors as the specific condition that is being treated, the severity of the condition, the duration of the treatment, the physical condition of the subject, the nature of any concurrent therapy, and the specific formulation and optional components utilized. However, a human patient in need of such treatment will typically receive from about 200 mg to about 2,000 mg of the antacid composition daily.

A further aspect of the present invention provides an acid-neutralizing coating and method for applying same to whole coffee beans. The coating of the present invention serves to preserve the flavor of coffee beans by sealing the bean against oxidation of the coffee oils after roasting and prior to brewing, and upon subsequent grinding and brewing results in the production of an acid-reduced coffee beverage. The coating of the present invention includes a water-soluble coating agent and an alkaline agent, i.e., a basic agent. The coating is applied to the coffee beans in an aqueous solution, and upon drying forms a hermetic seal on the exterior of the coffee bean. The coating is non-nutritious, meaning that it will not support substantial mold, fungal or bacterial growth.

The water-soluble coating agent or sealant included in the coating composition of the present invention is a water-soluble, edible polymer. A preferred coating agent suitable for use in the present invention is polyethylene glycol ("PEG"). PEG is commercially available in low or high molecular weights. Suitable preferred molecular weight PEGs for use in the present invention range from approximately 1,000 average molecular weight to 15,000 average molecular weight. A preferred PEG has an average molecular weight of 8,000 and is available from Union Carbide under the trademark CARBOWAX®. Other polymers that are water-soluble, substantially oxygen impervious, edible, and substantially non-nutritious may be utilized. Examples of additional coating agents include methoxypolyethylene glycol, ethylene oxide and potentially gums such as gum arabic, xanthan gum, agar and rosin. Polyethylene glycol is preferred because of its non-hydroscopic nature and because it does not deteriorate in the presence of alkaline environments. The coating agent is preferably included at a level of 1–5% by weight in an aqueous solution, more preferably 1–3% by weight, and most preferably approximately 3% by weight. For an 8,000 molecular weight polyethylene glycol, a most preferred concentration is 3% by weight.

The coffee bean coating composition of the present invention also includes an acid reducing alkaline agent. Suitable alkaline agents include alkaline earth metal carbonates, alkali metal hydroxides and alkaline earth metal hydroxides. A preferred acid reducing agent is an alkali metal hydroxide, and most preferably is potassium hydroxide, which is included at a level of 0.5–3% by weight in an aqueous solution, and more preferably at a level of approximately 1% by weight. In addition to or in lieu of potassium hydroxide, any of the of the previously described acid reducing compositions or the aforementioned embodiments for reducing acidity in brewed and ground coffees may be utilized as the acid reducing agent.

The coffee bean coating composition of the present invention may optionally also include an excipient such as sea salt or potassium chloride for enhanced flavor. A suitable level of sea salt or potassium chloride is approximately ½% by weight in the aqueous solution. Alternate excipients include sclareolide, a natural flavoring and mouth feel enhancer, included at a level of approximately 0.02%.

The coating solution of the present invention including the coating agent and alkaline agent in an aqueous solution is applied to the bean in an amount sufficient to create a sealing coating on the bean that contains sufficient acid-neutralizing agent to reduce the acidity of the ultimate brewed coffee beverage by a predetermined amount. When utilizing the preferred composition of 3% polyethylene glycol and 1% potassium hydroxide, the solution is applied to the beans in an amount sufficient to raise the weight of the dry bean by 3% while the solution is wet. After drying of the aqueous carrier, leaving only the coating and caustic agents and any other excipients, the weight of the dry bean is increased by approximately 1% relative to its pretreatment weight. The solution penetrates the exterior of the bean by a predetermined amount, suitably 0.010 to 0.020 inches.

Methods of applying the solution to the bean include soaking the beans in the solution, spraying the solution onto the beans and other methods, such as tumbling the beans in the solution utilizing a tablet coating machine. In order to apply the solution by soaking the beans, roasted coffee beans are cooled and then immersed in the coating solution. The beans are retained in the solution for a period of time sufficient to enable sufficient absorption of the coating, which preferably penetrates the surface of the bean to a depth of approximately 0.010–0.020", more preferably by approximately 0.015". At room temperature, this entails soaking for a period of approximately 2–3 minutes. The beans are then removed from the solution and dried to evaporate the water. Drying can occur at room temperature or, more preferably in an oven, operated at a temperature above ambient, such as 185–190° F.

The solution may alternately be applied by spraying onto the beans. Spraying may occur at any time after roasting, but preferably occurs immediately after roasting by incorporating the coating composition into the quench water used to cool the beans after roasting. Coffee beans are typically roasted at a temperature of 300–400° F. The beans are sprayed with a quenching solution consisting of the coating composition of the present invention in water, as described above. Most suitably, the beans are at a temperature of approximately 300° F. upon introduction of the quenching solution. The quenching solution cools the beans and the water from the solution concurrently dries, leaving cooled, coated dry beans. The application immediately after roasting is desirable because it prevents any degradation in the coffee oils, which tend to be forced to the surface of the bean during the roasting process.

While the acid reduced coating of the present invention has been described thus far as being added in a single step as a mixture, the acid reduced coating may alternately be added in two separate steps. Thus a solution of the acid reducing agent may first be applied to coffee beans, followed by drying, followed by application of a solution of the coating agent. This two step coating process may be preferred for coating agents that do not tolerate high alkaline environments well, such as certain gums.

Application of an acid reducing coating according to the present invention serves to reduce the acid of the roasted coffee bean, as well as the coffee beverage subsequently produced therefrom, without a detrimental affect on the taste and aroma of the coffee. The bitter acidic aftertaste sometimes associated with coffee is however eliminated.

Conventional coffee beans decline in quality after roasting. This is due to several factors. Coffee oils, forced to the surface of the bean during roasting by evaporating moisture within the bean, react to atmospheric oxygen and moisture and gradually go rancid. Additionally, roasted coffee beans contain several complex sugars. The brown color of roasted coffee comes from carmelization of these sugars. The oily and sugary outer surface of the coffee bean provides a nutritious media for atmospheric molds and fungi to grow. The coating composition of the present invention encapsulates the bean in a non-nutritious, thin coating that prevents the growth of mold or bacteria and fungi, as well as slowing the oxidation rate of the coffee oils. Finally, the desirable aroma of coffee that has been freshly roasted and brewed comes from the aromatic esters contained within the coffee. In conventional beans, these aromatic esters evaporate over time with storage, so that the aroma of coffee beans, as well as the flavor associated with these aromatic esters and associated odors, declines with time. The coating composition of the present invention substantially slows the evaporation of these aromatic esters, thereby preserving the aroma and flavor of freshly roasted coffee beans for a much longer period of time. These aromatic esters are subsequently released upon grinding and brewing of the coated coffee beans.

Coated coffee beans produced in accordance with the present invention can be blended with non-coated beans in a predetermined ratio to obtain a desired degree of acidity reduction. For example, coffee can be brewed from coffee beans which have been treated with the coating application of the present invention, or with a blend of coated beans and uncoated beans, to obtain a desired degree of reduced acidity which may, for example, be 5.7–6.1 pH.

In the single liquid process noted above, the ability to both reduce the acidity and also enhance the flavor of the coffee at the same time by adding flavor enhancers can be difficult. Certain desirable ingredients that can enhance the coffee flavor cannot survive in the high alkaline (suitably 12–13 pH) levels of the process solution.

An alternative embodiment of the present invention provides a two step coating process. First, roasted coffee beans are sprayed or dipped into an acid reducing liquid made up of a solvent such as water, an alkaline acid reducing agent which is preferably potassium hydroxide, and suitably also includes sea salt and potassium chloride. Other alkaline agents can be utilized in addition to potassium hydroxide as disclosed above. The beans are then totally dried by evaporating the water or other solvent.

Following the drying process, the beans are sprayed or dipped into a second liquid. The second liquid contains a solvent, such as water, and one or two types of agents: coating agent(s) that form a thin conformal shell around the coffee bean; and materials that improve the flavor or mouth feel. Preferably both coating agents and flavor enhancing agents are utilized.

Suitable coating agents include Gum Arabic, CMC, Polyethylene Glycol and other materials known in the pharmaceutical industry for enteric tablet coating. These materials form a shell around the coffee beans to extend the shelf life and reduce aromatic esters from dissipating.

Suitable flavor enhancing materials include sugars such as molasses and brown sugar (which provide a pleasant aftertaste), other substances such as scloroiide or other mouth feel enhancing additives known in the food industry.

Coating agents and flavor enhancing materials can be either water soluble or other solvents may instead be utilized.

Because the acid reducing liquid and the coating/flavor liquid are not mixed together during the process, the high alkaline level of the acid reducing liquid will not destroy the flavor enhancing materials. Suitable concentrations of acid reduction agents and coating agents are as disclosed above.

It is important to note that with this technique it is possible to improve the flavor of inferior tasting coffees such as the Robusta variety, and to improve the flavor of blends made with Robusta coffees. Therefore this two step process will widen the application field of this technology.

In a further aspect of the present invention, the acid neutralizing compositions described are also effective as lactose-reducing agents for milk and uncultured milk containing dairy products. The lactose reducing composition of the present invention preferably includes an alkali metal hydroxide and an alkaline earth metal hydroxide. A preferred alkali metal hydroxide is potassium hydroxide, while a preferred alkaline earth metal hydroxide is magnesium hydroxide. The lactose-reducing composition suitably also includes an alkaline earth metal carbonate, preferably calcium carbonate. In a preferred embodiment, calcium carbonate is included in the lactose-reducing composition in an amount ranging from 20 to 90% by weight of the total composition, potassium hydroxide is present in an amount ranging from 0.5 to 5% by weight of the total composition, and magnesium hydroxide in an amount ranging from 0.1 to 10% by weight of the total composition. The various alternate compositions set forth above for use in acid reduction are also believed to be suitable for lactose-reduction in accordance with this additional aspect of the present invention. Thus, as used herein the term lactose-reducing composition is intended to encompass the previously defined antacid or acid-neutralizing compositions.

The lactose-reduction composition of the present invention is added to milk, which may be whole milk, reduced fat milk, lowfat milk or fat-free milk, prior to consumption. The lactose-reducing composition can be added by the dairy producer to milk prior to homogenization and pasteurization, or by the consumer after homogenization and pasteurization. The lactose-reducing composition is suitably added in amounts sufficient to reduce the naturally occurring lactose in the milk by a predetermined amount, suitably by 50% or greater and more preferably by 75% or greater. The lactose-reducing composition of the present invention may be added at a level of 0.05 to 0.03% by weight, as determined by the dry lactose-reducing composition weight divided by the milk weight. A more preferred proportion is approximately 0.15% by weight of lactose-reducing composition based on the weight of the milk.

To aid in the dissolution of the lactose-reducing composition in the milk, the lactose-reducing composition may first be dissolved in an aqueous carrier. The aqueous solution is then added to milk, whereupon it is mixed during homogenization, followed by pasteurization. The liquid solution may alternately be added by the consumer prior to consuming the milk, because it results in a substantially instantaneous reduction in lactose. The lactose-reduced milk produced in accordance with the present invention may also be used to produce other lactose reduced dairy products, such as ice cream and puddings. The lactose-reduced milk produced in accordance with the present invention preserves the natural taste, flavor and mouthfeel of the milk without detrimental impact. An example of lactose-reduction using the preferred embodiment of the present invention is described below in Example 9.

The following examples further demonstrate and describe embodiments of the present invention. The examples are given solely for the purpose of illustration and not limitation.

EXAMPLES

Example 1

In this example, a representative acid-neutralizing composition of the present invention is described. A method for combining the ingredients and formulating the composition as a free-flowing granule is also described.

| Ingredient | Percent by Weight |
|---|---|
| Calcium carbonate | 66.82 |
| Potassium hydroxide | 7.25 |
| Magnesium hydroxide | 0.67 |
| Potassium chloride | 2.67 |
| Excipient | |
| Microcrystalline cellulose (Tabulose ™, Blenver Co., Brazil) | 5.33 |
| Carboxymethyl cellulose sodium (Solutab ™, Blenver Co., Brazil) | 16.75 |
| Vitamin D (dry stabilized vitamin $D_3$-water dispersible, Vitamins, Inc., Chicago, IL) | 0.17 |
| Instant coffee (Yuban ™) | 0.35 |

A granulated formulation having the above composition was prepared as described below. To a 20-quart mixing bowl was added 3675 grams calcium carbonate, 37 mgrams magnesium hydroxide, 147 grams potassium chloride, 293 grams Tabulose™, 921 grams Solutab™, and 9 grams vitamin $D_3$-water dispersible. The contents of the mixing bowl were mixed for approximately 5 minutes. While mixing, a solution of 399 grams potassium hydroxide in about 400 mL of deionized water was delivered over a period of about 2 minutes to the mixed solids in the mixing bowl by way of a peristaltic pump. Upon the completion of the addition of the potassium hydroxide solution, the blend was mixed for an additional ten minutes. A solution of 19 grams instant coffee (Yuban™) in 1200 mL deionized water (prepared from the addition of 1200 mL hot deionized water to 19 grams instant coffee) was then delivered over a period of about 4.5 minutes to the mixed solids in the mixing bowl by way of a peristaltic pump. Upon the completion of the addition of the instant coffee solution, the blend was mixed for an additional five minutes. At this point, 100 to 200 mL additional water may be added to the blend, if necessary, to provide a mixture having a granular (i.e., nonpowdery) appearance. The moist formula was then mixed for approximately 20 minutes with occasional wiping of the sides of the mixing bowl with a spatula to assure a thorough mixing of the entire formula. After thorough mixing, the moist formula was transferred into a large plastic bin. The contents of the bin were then added in portions to fill the funnel of a cutting machine. The cutting machine and the auger were then powered on and the formula was granulated. After granulation, the cutting machine and auger were powered off and the granulated formula was collected using a vacuum. The granulated formula was then distributed to oven trays (approximately one pound of formula per tray), the trays were placed in an oven, and the formula dried for 30 minutes at a temperature of 180° F. The trays of formula were then rotated in the oven to assure uniform heat treatment, and dried for an additional 30 minutes. Removal from the oven and cooling provided a representative composition of the present invention formulated as a free-flowing granule.

Example 2

In this example, another representative acid-neutralizing composition of the present invention is described.

| Ingredient | Percent by Weight |
|---|---|
| Calcium carbonate | 63.33 |
| Potassium hydroxide | 11.64 |
| Magnesium hydroxide | 6.14 |
| Potassium chloride | 2.33 |
| Excipient | |
| Microcrystalline cellulose (Tabulose ™, Blenver Co., Brazil) | 6.19 |
| Carboxymethyl cellulose sodium (Solutab ™, Blenver Co., Brazil) | 8.91 |
| Vitamin D (dry stabilized vitamin $D_3$-water dispersible, Vitamins, Inc., Chicago, IL) | 0.47 |
| Magnesium stearate | 1.01 |

These ingredients were combined to provide a composition that is a free-flowing granule by the method described above in Example 1.

Example 3

In this example, a representative acid-neutralizing composition of the present invention including gelatin and bacteria and fungi retarder is described.

| Ingredient | Percent by Weight |
|---|---|
| Calcium carbonate | 62.10 |
| Potassium hydroxide | 11.42 |
| Magnesium hydroxide | 6.02 |
| Potassium chloride | 2.28 |
| Foodgrade type B gelatin | 1.83 |
| Bacteria and fungi retarder | |
| Methyl paraben | 0.02 |
| Propyl paraben | 0.08 |
| Excipient | |
| Microcrystalline cellulose (Tabulose ™, Blenver Co., Brazil) | 6.07 |
| Carboxymethyl cellulose sodium (Solutab ™, Blenver Co., Brazil) | 8.74 |
| Vitamin D (dry stabilized vitamin $D_3$-water dispersible, Vitamins, Inc., Chicago, IL) | 0.46 |
| Magnesium stearate | 1.00 |

These ingredients were combined to provide a composition that is a free-flowing granule by the method described above in Example 1.

Example 4

In this example, tests evaluating the taste of coffees prepared by the methods of the present invention are described. In these tests, the taste of coffees containing embodiments of the acid-neutralizing compositions of this invention was evaluated by coffee tasters and compared with the taste of plain coffee (i.e., the same coffee containing no acid-neutralizing composition).

In the tests, the coffee tasters rated each of nine categories on a scale from 1 (worst) to 5 (best). The categories evaluated were aroma, appearance, acidic taste, chemical taste, salt taste, sweetness, bitterness, aftertaste, and overall impression.

The following acid-neutralizing composition formulations were tested:

Formulation A 567 grams calcium carbonate 28.4 grams FMA-11™ (a mixture consisting of 41.5 weight percent aluminum hydroxide, 8.0 weight percent magnesium hydroxide, 50.5 weight
percent calcium carbonate; Reheis Corp., Berkeley Heights, N.J.)
  6 grams potassium chloride
  6 grams gelatin
Formulation B
  143.5 grams calcium carbonate
  3.5 grams FMA-11™
  1.8 grams aluminum hydroxide
  1.5 grams potassium chloride
Formulation C
  143.5 grams calcium carbonate
  3.5 grams FMA-11™
  1.8 grams magnesium carbonate
  1.5 grams potassium chloride
Formulation D
  140.3 grams calcium carbonate
  7.1 grams FMA-11™
  3 grams potassium chloride
Formulation E
  138.8 grams calcium carbonate
  7.1 grams FMA-11™
  4.5 grams potassium chloride
Formulation F
  137.3 grams calcium carbonate
  7.1 grams FMA-11™
  6 grams potassium chloride Each of the test coffee samples was prepared by the addition of 1.4 grams of one of the above formulations to a 12-cup pot of brewed coffee Millstone Breakfast Blend™.

The taste test results are summarized in the following table. Average score refers to the average overall taste on a scale from 1 (worst) to 5 (best).

| Formulation | Average score |
| --- | --- |
| Plain coffee | 3.8 (2.75) |
| A | 3.8 (2.34) |
| B | 4.3 (3.00) |
| C | 3.6 (2.88) |
| D | 3.9 (2.86) |
| E | 3.4 |
| F | 3.1 |

The values represent an average of the values assigned by eight taste testers in the age group of 25 to 35 years old.

The values in parentheses represent the results of a subsequent taste test by eight taste testers in the age group of 55 to 75 years old.

As summarized in the table above, several acid-neutralizing composition formulations were found to have tastes more pleasing than plain coffee. In the taste tests, Formulation B was determined to be the most flavorful coffee.

Example 5

Representative Antacid Compositions

In this Example, representative antacid compositions of the invention (i.e., Formulations G-P) are described. Formulations G-P were prepared by combining the ingredients tabulated below in the amounts specified and formulating the resulting mixture as a free-flowing granule as described above in Example 1.

The following antacid composition formulations were prepared:

Formulation G:

| Ingredient | Percent by Weight |
| --- | --- |
| Calcium carbonate | 72.0 |
| Potassium hydroxide | 5.0 |
| Magnesium hydroxide | 0.7 |
| Excipients | |
| Microcrystalline cellulose | 20.3 |
| Croscarmellose sodium NF | 2.0 |

Formulation H:

| Ingredient | Percent by Weight |
| --- | --- |
| Calcium carbonate | 46.51 |
| Potassium hydroxide | 3.80 |
| Magnesium hydroxide | 4.07 |
| Excipient | |
| Croscarmellose sodium NF | 2.01 |
| Microcrystalline cellulose | 20.07 |
| Silicon dioxide | 0.50 |
| Flavoring agents | |
| Natural spearmint flavor | 2.71 |
| Fructose | 20.34 |

Formulation I:

| Ingredient | Percent by Weight |
| --- | --- |
| Calcium carbonate | 45.28 |
| Potassium hydroxide | 3.70 |
| Magnesium hydroxide | 3.96 |
| Excipient | |
| Croscarmellose sodium NF | 1.95 |
| Microcrystalline cellulose | 19.54 |
| Silicon dioxide | 0.48 |
| Flavoring agents | |
| Natural spearmint flavor | 5.28 |
| Fructose | 19.80 |

Formulation J:

| Ingredient | Percent by Weight |
| --- | --- |
| Calcium carbonate | 45.74 |
| Potassium hydroxide | 3.73 |
| Magnesium hydroxide | 4.00 |
| Excipient | |
| Croscarmellose sodium NF | 2.03 |
| Microcrystalline cellulose | 20.00 |
| Silicon dioxide | 0.50 |
| Flavoring agents | |
| Natural spearmint flavor | 5.33 |
| Sucrose | 18.67 |

Formulation K:

| Ingredient | Percent by Weight |
|---|---|
| Calcium carbonate | 41.44 |
| Potassium hydroxide | 3.38 |
| Magnesium hydroxide | 3.62 |
| Excipient | |
| Croscarmellose sodium NF | 2.05 |
| Microcrystalline cellulose | 20.05 |
| Silicon dioxide | 0.45 |
| Flavoring agents | |
| Natural spearmint flavor | 4.83 |
| Sucrose | 24.16 |

Formulation L:

| Ingredient | Percent by Weight |
|---|---|
| Calcium carbonate | 31.55 |
| Potassium hydroxide | 1.61 |
| Magnesium hydroxide | 2.68 |
| Excipient | |
| Croscarmellose sodium NF | 2.05 |
| Microcrystalline cellulose | 20.54 |
| Silicon dioxide | 0.50 |
| Flavoring agents | |
| Natural spearmint flavor | 5.36 |
| Sucrose | 35.71 |

Formulation M:

| Ingredient | Percent by Weight |
|---|---|
| Calcium carbonate | 28.19 |
| Potassium hydroxide | 1.44 |
| Magnesium hydroxide | 2.39 |
| Excipient | |
| Croscarmellose sodium NF | 2.00 |
| Microcrystalline cellulose | 20.00 |
| Silicon dioxide | 0.51 |
| Flavoring agents | |
| Natural spearmint flavor | 5.58 |
| Sucrose | 39.88 |

Formulation N:

| Ingredient | Percent by Weight |
|---|---|
| Calcium carbonate | 28.57 |
| Potassium hydroxide | 1.60 |
| Magnesium hydroxide | 1.50 |
| Excipient | |
| Croscarmellose sodium NF | 5.51 |
| Microcrystalline cellulose | 20.00 |
| Silicon dioxide | 0.50 |
| Flavoring agents | |
| Natural spearmint flavor | 7.71 |
| Sucrose | 34.60 |

Formulation O:

| Ingredient | Percent by Weight |
|---|---|
| Calcium carbonate | 29.40 |
| Potassium hydroxide | 1.60 |
| Magnesium hydroxide | 1.50 |
| Excipient | |
| Croscarmellose sodium NF | 4.00 |
| Microcrystalline cellulose | 20.00 |
| Silicon dioxide | 0.50 |
| Flavoring agents | |
| Natural spearmint flavor | 8.5 |
| Sucrose | 34.50 |

The acid-neutralizing effectiveness of the representative antacid compositions of this example is described in Example 6.

Example 6

Acid-Neutralizing Effectiveness of Representative Antacid Compositions

This Example describes the acid-neutralizing effectiveness of representative antacid compositions (i.e., Formulations G–N) prepared as described in Example 5 above. In each neutralization experiment, 300 mg of an antacid tablet was crushed into a powder and added to a 100 gram solution of aqueous hydrochloric acid having a pH of about 1.8. The pH of the continuously stirred solution was measured prior to the addition of the antacid and then every minute for ten minutes after the antacid addition.

The pH values of the solutions as a function of time are presented in the table below.

| Antacid Effectiveness: Change in pH over time Formulation | | | | | | | | |
|---|---|---|---|---|---|---|---|---|
| Time (min.) | G | H | I | J | K | L | M | N |
| 0 | 1.57 | 1.73 | 1.75 | 1.38 | 1.25 | 1.93 | 1.95 | 1.95 |
| 1 | 6.45 | 8.28 | 8.64 | 9.23 | 9.14 | 8.76 | 7.73 | 8.05 |
| 2 | 7.66 | 9.13 | 9.47 | 9.51 | 9.55 | 9.26 | 8.84 | 8.95 |
| 3 | 8.73 | 9.59 | 9.89 | 9.59 | 9.68 | 9.63 | 9.20 | 9.31 |
| 4 | 9.11 | 9.86 | 10.16 | 9.63 | 9.74 | 9.80 | 9.40 | 9.57 |
| 5 | 9.3 | 10.07 | 10.34 | 9.66 | 9.78 | 9.89 | 9.56 | 9.77 |
| 6 | 9.48 | 10.23 | 10.52 | 9.69 | 9.80 | 9.96 | 9.66 | 9.91 |
| 7 | 9.54 | 10.36 | 10.59 | 9.73 | 9.87 | 10.06 | 9.79 | 10.05 |
| 8 | 9.61 | 10.45 | 10.68 | 9.75 | 9.89 | 10.14 | 9.88 | 10.18 |
| 9 | 9.66 | 10.54 | 10.74 | 9.79 | 9.92 | 10.24 | 9.97 | 10.27 |
| 10 | 9.73 | 10.61 | 10.8 | 9.81 | 9.95 | 10.35 | 10.04 | 10.35 |

The results show that when added to an acidic solution the representative antacid compositions of the invention rapidly achieve a high level of acid neutralization (i.e., pH 8–9 after 1 to 2 minutes). Final pH values of about 10 are attained for the treated solutions shortly thereafter.

Example 7

Comparison of Antacid Effectiveness of Invention Relative to Commercial Antacids The acid-neutralizing effectiveness for a representative antacid composition of the invention (Formulation N from Example 6) was compared to several commercially available, over-the-counter antacid compositions. The commercially available antacids used in the comparison included:

| Antacid | Active Ingredients |
| --- | --- |
| MYLANTA (Johnson & Johnson/Merck, Fort Washington, PA) | Calcium carbonate, magnesium hydroxide |
| GAVISCON (Smith Kline Beecham, Pittsburgh, PA) | Aluminum hydroxide, sodium bicarbonate |
| TUMS E-X (Smith Kline Beecham, Pittsburgh, PA) | Calcium carbonate |
| MAALOX (Rhone-Poulenc Rover Pharmaceuticals Inc. Collegeville, PA) | Aluminum hydroxide, magnesium hydroxide |
| ROLAIDS (Warner-Lambert Co., Morris Plains, NJ) | Calcium carbonate, magnesium hydroxide |
| MEDACID (Bristol-Meyers Squibb Co., New York, NY) | Calcium carbonate, magnesium carbonate, magnesium oxide |
| PRELIEF (AkPharma Inc., El Paso, TX) | Calcium glycerin phosphate |

In these comparative experiments, 300 mg of each antacid was crushed and added to 100 g of an aqueous hydrochloric acid solution (0.015 M HCl, pH 1.80) with stirring. The pH of the continuously stirred solution was monitored over time (i.e., pH measured prior to addition of antacid and then every minute for ten minutes after antacid addition) to determine the rate of acid neutralization as well as the extent to which each antacid neutralized the acidic solution (i.e., the final pH of the solution). The results of acid-neutralizing experiments comparing a representative antacid composition of this invention (i.e., Formulation N) to the commercially available antacids MYLANTA, GAVISCON, TUMS E-X, MAALOX, ROLAIDS, MEDACID, and PRELIEF are graphically illustrated in FIG. 1.

The representative antacid composition of the present invention is the fastest acting of the antacids compared. Referring to FIG. 1, the results show that after one minute, the representative antacid composition of the invention reduced the acidity of the aqueous solution and elevated its pH to about 9. For the commercial antacids, after one minute, PRELIEF raised the pH of the solution to about 7.5, MEDACID, ROLAIDS, TUMS, and MYLANTA raised the pH of the solution to between about 4 to 5, while MAALOX and GAVISCON showed little effect of the solution's pH. The rapid rate of acid neutralization exhibited by the antacid of the invention is the greatest of the antacids compared.

Referring to FIG. 1, at the four-minute time point, only MEDACID had neutralized the acidic solution to the same extent as the representative antacid composition of this invention (i.e., pH about 10). Solutions containing PRELIEF, ROLAIDS, TUMS, and MYLANTA had pH values between about 5 to 7, and the acidity of solutions treated with MAALOX and GAVISCON remain essentially unchanged (i.e., pH about 2 to 3). After ten minutes, acid neutralization appeared nearly complete. The antacid composition of the invention provides a solution having a final pH of about 10.5, MEDACID about pH 10.5, ROLAIDS about pH 10, MYLANTA about pH 8.5, PRELIEF about pH 7.5, TUMS about pH 7, MAALOX about pH 3, and GAVISCON about pH 2.5.

Referring to FIG. 1, it appears that generally the rapid acid-neutralizing action of the antacid compositions may be attributed their rapid acting components: potassium hydroxide and magnesium hydroxide for the antacid of this invention; magnesium oxide for MEDACID; magnesium hydroxide for ROLAIDS and MYLANTA; and calcium glycerol phosphate for PRELIEF. Referring to FIG. 1, the secondary neutralizing effect exhibited by the antacid compositions of the present invention, and MEDACID, ROLAIDS, and MYLANTA may be attributed to calcium carbonate, their long-lasting antacid component. The acid neutralization curves for TUMS and PRELIEF reflect their having a single acid-neutralizing ingredient. The aluminum hydroxide containing antacids, GAVISCON and MAALOX, appear to be the least effective in neutralizing acid of all the antacids compared.

Example 8

Comparison of Antacid Effectiveness of the Invention and Commercial Antacids on a Weight Basis In a comparative experiment, powdered antacids were added to 150 grams of an aqueous solution of hydrochloric acid (pH 3.0) with stirring. For each solution, powdered antacid was added until the pH of the solution was raised to pH 6.0. In the experiment, each portion of added antacid was allowed to dissolve and establish the pH before the next portion was added.

Figure 2:
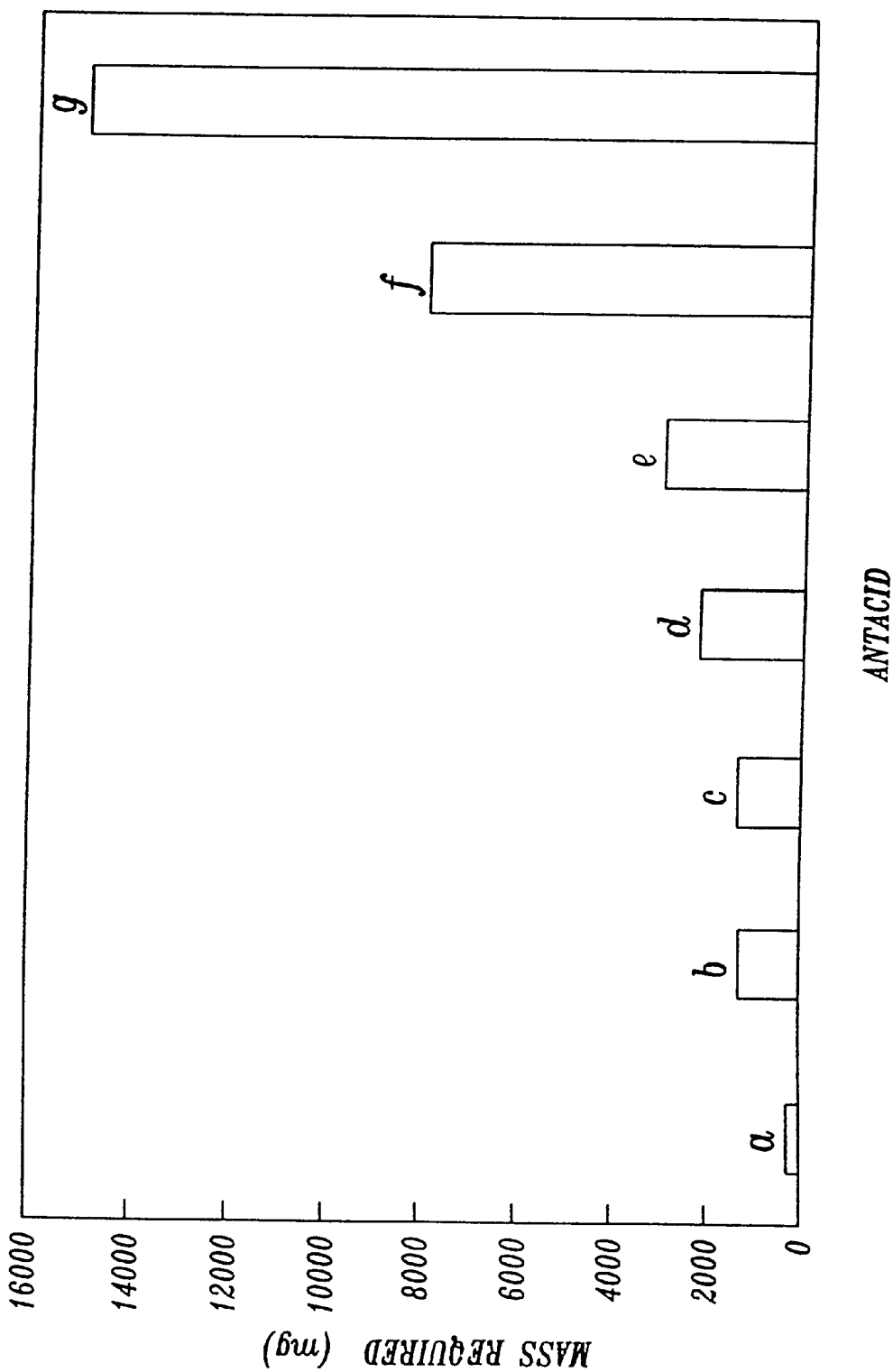
FIG. 2 is a bar graph comparing the weight effectiveness in adjusting the pH of a solution from pH 3.0 to pH 6.0 with a representative antacid composition of the present invention (a) and several commercially available antacids: ROLAIDS (b), MYLANTA (c), TUMS (d), MAALOX (e), CVS (f), and GAVISCON (g).

The results, summarized below and graphically illustrated in FIG. 2, demonstrate that the representative antacid composition of the present invention (Formulation N from Example 6) is more potent than the commercially available antacids compared on a weight basis. The representative antacid, Formulation N, was about 5 times more potent than ROLAIDS, nearly 10 times more potent than TUMS, and more than 50 times more potent than GAVISCON. It is also noted that the deacidifier composition of Example I may be used as an antacid, and when subjected to the comparative testing of the present example, only 195 mg is required for the desired neutralizing effect.

| Antacid | Antacid Potency by Weight Amount Antacid Added (mg) | Relative Potency |
| --- | --- | --- |
| Formulation N | 245 | 1.00 |
| ROLAIDS | 1,271 | 0.19 |
| MYLANTA | 1,372 | 0.18 |
| TUMS | 2,190 | 0.11 |
| MAALOX | 3,007 | 0.08 |
| CVS | 6,427 | 0.04 |
| GAVISCON | 15,000 | 0.02 |

Example 9

Comparison of Lactose Reduction Effectiveness of the Invention and Commercial Lactose-Reducing Enzymes Lactose-reducing composition formulated in accordance with Example 1 above, containing 66.82% calcium carbonate, 7.25% potassium hydroxide, 0.67% magnesium hydroxide, 2.67% potassium chloride and balance excipient was added to 1% milkfat milk, at a level of 320 milligrams of dry composition per one 8 ounce cup of milk. This corresponds to approximately 0.135% by weight of the lactose-reducing compound in the milk. This lactose-reduced milk in accordance with the present invention was compared to a control sample, consisting of untreated 1% milkfat milk, and to a conventional lactase enzyme reduced 1% milkfat milk. A portion of the control sample was utilized as the milk to which the lactose reducing composition of the present invention was added, so that the initial lactose content of the control milk and the treated milk were the same prior to the addition of the lactose reducing composition of the present invention. The lactase enzyme treated milk had an unknown initial lactose content, but is labeled for retail sales as having a 70% reduced lactose content.

These three milks, i.e., untreated control, lactose-reduced milk in accordance with the present invention, and enzyme treated milk, were subjected to two different analysis. The first of these is an analysis of the freezing point depression of the milk product, which typically is indicative of the amount of lactose hydrolysis caused by enzyme treatment. The three samples were also subjected to a high pressure liquid chromatography (HPLC) analysis to determine the amount of lactose monohydrate contained in the milk. The results of this testing are as follows:

| Milk Sample | Freezing Point Depression | HPLC Peak Corresponding To Percent Lactose Monohydrate |
|---|---|---|
| Untreated Control 1% milkfat milk | 540% | 5.11 |
| Lactose-reduced milk in accordance with the present invention | 550% | 4.71 |
| Enzyme-treated milk | 730% | 5.19 |

The freezing point was not significantly depressed by treatment of milk utilizing the composition of the present invention, indicating that the product maintains an ionic equilibrium very close to untreated milk. This is compared to the enzyme-treated milk, which exhibited freezing point depression indicative of lactose hydrolysis. The high pressure liquid chromatography analysis indicated that the composition of the present invention did result in reduction of lactose, by an amount equating to approximately an 80% reduction of lactose relative to the control sample. This then was a 10% greater lactose reduction than the 70% reduction claimed for the commercially enzyme treated milk. The HPLC reading for the enzyme treated milk was higher than the control sample presumably due to a higher unknown initial lactose content before enzyme treatment.

In summary, the antacid compositions of this invention are the most rapid acting and provide the greatest acid neutralization of all the commercial antacids compared.

While the preferred embodiment of the invention has been illustrated and described, it will be apparent that various changes can be made therein without departing from the spirit and scope of the invention.

The embodiments of the invention in which an exclusive property or privilege is claimed are defined as follow:

1. An acid reduced coffee product, comprising:
   roasted coffee beans; and
   an acid reducing coating applied to the exterior of the roasted coffee beans, comprising:
      an alkaline agent; and
      a coating agent.
2. The acid reduced coffee product of claim 1, wherein the alkaline agent comprises potassium hydroxide.
3. The acid reduced coffee product of claim 1, wherein the coating agent comprises polyethylene glycol.
4. The acid reduced coffee product of claim 1, wherein the coating agent comprises gum arabic.
5. The acid reduced coffee product of claim 1, wherein the coating agent comprises carboxymethyl cellulose.
6. The acid reduced coffee product of claim 1, wherein the alkaline agent comprises potassium hydroxide and the coating agent comprises gum arabic.
7. An acid reduced coffee product, comprising:
   roasted coffee beans; and
   an acid reducing coating applied to the exterior of the roasted coffee beans, comprising:
      (a) an alkaline agent;
      (b) sodium chloride; and
      (c) a coating agent.
8. The acid reduced coffee product of claim 7, wherein the alkaline agent comprises potassium hydroxide.
9. The acid reduced coffee product of claim 7, wherein the alkaline agent comprises potassium hydroxide in an amount sufficient to produce a brewed coffee with a pH of about 5.7 to 6.3.
10. The acid reduced coffee product of claim 7, wherein the coating agent comprises gum Arabic.
11. An acid reduced coffee product, comprising:
   roasted coffee beans; and
   an acid reducing coating applied to the exterior of the roasted coffee beans, comprising:
      (a) an alkaline agent, wherein the alkaline agent is at least one of an alkali metal hydroxide and an alkaline earth metal hydroxide; and
      (b) a coating agent.
12. The acid reduced coffee product of claim 11, wherein the alkaline agent comprises potassium hydroxide.
13. The acid reduced coffee product of claim 11, wherein the alkaline agent comprises potassium hydroxide in an amount sufficient to produce a brewed coffee with a pH of about 5.7 to 6.3
14. The acid reduced coffee product of claim 11, wherein the coating agent comprises gum Arabic.

* * * * *

UNITED STATES PATENT AND TRADEMARK OFFICE
CERTIFICATE OF CORRECTION

PATENT NO. : 6,495,180 B1
DATED : December 17, 2002
INVENTOR(S) : I.M. Gurol

Page 1 of 1

It is certified that error appears in the above-identified patent and that said Letters Patent is hereby corrected as shown below:

<u>Column 28,</u>
Lines 18 and 23, "arabic." should read -- Arabic. --
Line 54, "6.3" should read -- 6.3. --

Signed and Sealed this

Second Day of December, 2003

JAMES E. ROGAN
*Director of the United States Patent and Trademark Office*